(12) United States Patent
Bierman

(10) Patent No.: US 6,283,945 B1
(45) Date of Patent: Sep. 4, 2001

(54) ANCHORING SYSTEM FOR A MEDICAL ARTICLE

(75) Inventor: Steven F. Bierman, Del Mar, CA (US)

(73) Assignee: Venetec International, Inc., San Diego, CA (US)

( * ) Notice: Subject to any disclaimer, the term of this patent is extended or adjusted under 35 U.S.C. 154(b) by 0 days.

(21) Appl. No.: 09/049,825

(22) Filed: Mar. 27, 1998

Related U.S. Application Data

(60) Provisional application No. 60/062,323, filed on Oct. 17, 1997.

(51) Int. Cl.$^7$ .................................................... A61M 5/32
(52) U.S. Cl. ................................. 604/174; 128/DIG. 26
(58) Field of Search ........................... 604/174, 178–180, 604/903; 128/877, DIG. 26; 248/74.1–74.3, 205.1, 205.3

(56) References Cited

U.S. PATENT DOCUMENTS

| | | |
|---|---|---|
| D. 364,922 * | 12/1995 | Bierman . |
| D. 375,355 | 11/1996 | Bierman . |
| 2,525,398 | 10/1950 | Collins . |
| 2,707,953 | 5/1955 | Ryan . |
| 3,059,645 | 10/1962 | Hasbrouck et al. . |
| 3,064,648 | 11/1962 | Bujan . |
| 3,482,569 | 12/1969 | Raffaelli, Sr. . |
| 3,630,195 | 12/1971 | Santomieri . |
| 3,677,250 | 7/1972 | Thomas . |
| 3,766,915 | 10/1973 | Rychlik . |
| 3,856,020 | 12/1974 | Kovac . |
| 3,896,527 * | 7/1975 | Miller et al. ............................ 24/499 |
| 3,906,946 | 9/1975 | Nordström . |
| 3,973,565 | 8/1976 | Steer . |
| 4,020,835 | 5/1977 | Nordstrom et al. . |
| 4,057,066 | 11/1977 | Taylor . |
| 4,059,105 | 11/1977 | Cutruzzula et al. . |
| 4,129,128 | 12/1978 | McFarlane . |

(List continued on next page.)

FOREIGN PATENT DOCUMENTS

| | | |
|---|---|---|
| 0064284 A2 | 10/1982 | (EP) . |
| 356683 A | 3/1990 | (EP) . |
| 2381529 | 9/1978 | (FR) . |
| 2288542A | 10/1995 | (GB) . |
| WO 92/19309 | 11/1992 | (WO) . |

Primary Examiner—Anhtuan T. Nguyen
(74) Attorney, Agent, or Firm—Knobbe, Martens, Olson & Bear, LLP

(57) ABSTRACT

An anchoring system secures a catheter to the body of a patient and arrests axial movement of the catheter without meaningfully impairing fluid flow through the catheter. The anchoring system includes an anchor pad that adheres to the patient's skin and supports a retainer. The retainer releasably receives a portion of the catheter and includes one or more retention mechanisms. The retention mechanisms inhibit axial movement of the catheter relative to the retainer when the catheter is secured therein. In one mode, the retention mechanism is positioned within a channel of the retainer and includes at least first and second members that project from opposite sides of the channel. The members are arranged to cooperate with one another when the cover is closed so as to capture a structural portion of the catheter between the first and second members without substantially occluding an inner lumen of the catheter.

58 Claims, 6 Drawing Sheets

U.S. PATENT DOCUMENTS

| | | |
|---|---|---|
| 4,133,307 | 1/1979 | Ness .................................... 602/32 |
| 4,161,177 | 7/1979 | Fuchs . |
| 4,193,174 | 3/1980 | Stephens . |
| 4,224,937 | 9/1980 | Gordon . |
| 4,248,229 | 2/1981 | Miller . |
| 4,250,880 | 2/1981 | Gordon . |
| 4,316,461 | 2/1982 | Marais et al. . |
| 4,326,519 | 4/1982 | D'Alo et al. . |
| 4,362,156 | 12/1982 | Feller, Jr. et al. . |
| 4,392,853 | 7/1983 | Muto . |
| 4,397,647 * | 8/1983 | Gordon ............................ 604/180 |
| 4,449,975 | 5/1984 | Perry . |
| 4,453,933 | 6/1984 | Speaker . |
| 4,480,639 | 11/1984 | Peterson et al. . |
| 4,711,636 | 12/1987 | Bierman . |
| 4,742,824 | 5/1988 | Payton et al. . |
| 4,808,162 | 2/1989 | Oliver . |
| 4,852,844 | 8/1989 | Villaveces . |
| 4,857,058 | 8/1989 | Payton . |
| 4,863,432 | 9/1989 | Kvalo . |
| 4,897,082 | 1/1990 | Erskine . |
| 4,898,587 * | 2/1990 | Mera . |
| 4,919,654 * | 4/1990 | Kalt . |
| 4,955,864 * | 9/1990 | Hajduch . |
| 4,976,700 * | 12/1990 | Tollini . |
| 5,037,397 * | 8/1991 | Kalt et al. . |
| 5,073,170 * | 12/1991 | Schneider . |
| 5,084,026 * | 1/1992 | Shapiro . |
| 5,098,399 * | 3/1992 | Tollini . |
| 5,147,322 * | 9/1992 | Bowen et al. . |
| 5,156,641 * | 10/1992 | White . |
| 5,192,273 * | 3/1993 | Bierman et al. . |
| 5,192,274 * | 3/1993 | Bierman . |
| 5,195,981 * | 3/1993 | Johnson . |
| 5,266,401 * | 11/1993 | Tollini . |
| 5,292,312 * | 3/1994 | Delk et al. . |
| 5,304,146 * | 4/1994 | Johnson et al. . |
| 5,306,243 * | 4/1994 | Bonaldo . |
| 5,314,411 * | 5/1994 | Bierman . |
| 5,338,308 * | 8/1994 | Wilk . |
| 5,342,317 * | 8/1994 | Claywell . |
| 5,344,406 * | 9/1994 | Spooner . |
| 5,354,282 * | 10/1994 | Bierman . |
| 5,368,575 | 11/1994 | Chang . |
| 5,380,293 * | 1/1995 | Grant . |
| 5,389,082 | 2/1995 | Baugues et al. . |
| 5,398,679 | 3/1995 | Freed . |
| 5,403,285 * | 4/1995 | Roberts . |
| 5,413,562 * | 5/1995 | Swauger . |
| 5,443,460 * | 8/1995 | Miklusek . |
| 5,456,671 * | 10/1995 | Bierman . |
| 5,468,231 * | 11/1995 | Newman et al. . |
| 5,470,321 * | 11/1995 | Forster et al. . |
| 5,496,282 * | 3/1996 | Militzer et al. . |
| 5,496,283 * | 3/1996 | Alexander . |
| 5,499,976 * | 3/1996 | Dalton . |
| 5,520,656 | 5/1996 | Byrd . |
| 5,527,293 | 6/1996 | Zamierowski . |
| B1 5,147,322 * | 1/1996 | Bowen et al. . |

\* cited by examiner

LATERAL

LOGITUDNAL

US 6,283,945 B1

ANCHORING SYSTEM FOR A MEDICAL ARTICLE

RELATED APPLICATION

This application claims the benefit of priority under 35 U.S.C. § 119(e) of provisional application Serial. No. 60/062,323, filed Oct. 17, 1997.

BACKGROUND OF THE INVENTION

1. Field on the Invention

The present invention relates to an anchoring system for securing a medical article to a patient to inhibit movement or migration of the medical article relative to the patient.

2. Description of Related Art

Hospitalized patients often have limited mobility due either to their condition or to doctor's orders. Such patients must lie in bed and not move about their hospital room, even to urinate. As such, a Foley catheter is often used with the bed-confined patient to drain urine from the patient's bladder. Use of a Foley catheter thus eliminates toilet trips as well as reduces bedpan use.

A Foley catheter typically includes two coaxial lumens: a drainage lumen and an inflation lumen. The inflation lumen communicates with an inflation balloon located at the tip of the catheter (i.e., the catheter proximal end). The proximal end of the drainage lumen includes one or more influent openings to receive urine from the bladder. The lumens usually diverge in a Y-type pattern at the distal end of the catheter to form an effluent port and an inflation port.

In use, a healthcare provider inserts the Foley catheter through the urinary tract of the patient to locate the tip of the catheter within the patient's bladder. Although the catheter usually includes a siliconized outer coating as provided by the manufacturer, healthcare providers often apply further lubricant, such as, for example, water-based jelly. The provider then inflates the balloon by attaching the inflation port to a source of pressurized working fluid (e.g., saline solution). Once inflated, a valve, which is located at the inflation port, inhibits the flow of fluid from the inflation lumen and the balloon to keep the balloon inflated. The inflated balloon prevents the catheter from unintentionally dislodging from the bladder. The healthcare provider then connects the distal end of the drainage lumen (i.e., its effluent port) to a drainage tube leading to a collection container.

The healthcare provider usually secures the distal end of the Foley catheter to the patient using tape. That is, the healthcare provider commonly places long pieces of tape across the distal end of the catheter in a crisscross pattern to secure the catheter distal end to the inner thigh of the patient. This securement inhibits disconnection between the catheter and the drainage tube, as well as prevents the catheter or drainage tube from snagging on the bed rail or other object.

Taped connections, however, often collect contaminates and dirt. Normal protocol therefore requires periodic (e.g., daily) tape changes in order to inhibit bacteria and germ growth at the securement site. Frequent tape changes though lead to another problem: excoriation of the patient's skin. In addition, valuable time is spent applying and reapplying the tape to secure the catheter. And healthcare providers often remove their gloves when taping because most find the taping procedure difficult and cumbersome when wearing gloves. Not only does this further lengthen the procedure, but it also subjects the healthcare provider to possible infection.

A number of catheter securement devices have been developed to obviate the need for frequent application of tape. U.S. Pat. Nos. 5,304,146 and 5,342,317 disclose several examples of such devices. Although these devices hold the catheter to the patient, they fail to arrest longitudinal movement of the catheter. These devices rely upon friction between the catheter and a band wrapped over the catheter to prevent axial movement. Such contact between the catheter and the securement device, however, often fails to arrest axial movement of the catheter, especially when used with a lubricated catheter (e.g., a Foley catheter).

Other securement devices have attempted to improve the securement of Foley catheters. One such securement device is disclosed in U.S. Pat. No. 4,397,647. The approach taught by this patent, however, at least partially occludes the catheter and prevents the free flow of urine through the catheter. Improper drainage of the bladder consequently may occur, leading to patient discomfort and possible medical complications (e.g., infection).

A need therefore exists for a simply-structured anchoring system that secures a catheter to a patient, without occluding or otherwise restricting fluid flow through the catheter.

SUMMARY OF THE INVENTION

One aspect of the present invention thus involves an anchoring system for securing a medical article to the body of a patient. The system comprises an anchor pad having an upper surface and a lower surface. The lower surface has an adhesive layer which adheres to the body of a patient. A retainer is mounted onto the upper surface of the anchor pad and receives a portion of the medical article. The retainer is formed by a base and a cover. The base has a first side and a second, opposite side. The base also includes a groove having a curvilinear cross-sectional shape. The cover is formed in a similar manner as the base. The first side of the cover attaches to the first side of the base and the second side of the cover is moveable between a closed position, in which the second side of the cover lies generally above the second side of the base, and an open position, in which the second side of the cover is spaced apart from the second side of the base so as to expose the groove in the base. When the cover is closed, the grooves in the base and cover define a channel having a curvilinear cross-sectional shape. The cross-sectional area of the channel varies over the length of the channel. Also, a latching mechanism, which is operable between the base and the cover, releasably secures the second side of the cover to the second side of the base.

Another aspect of the present invention involves an anchoring system including an anchor pad with an upper surface and a lower surface. At least a portion of the lower surface is formed with an adhesive layer for attachment to the patient's skin. A retainer is permanently affixed to the upper surface of the anchor pad and comprises a base and a cover. The base has a first groove to receive at least a portion of an elongated medical article. The cover is pivotally coupled to the base and moveable between an open position and a closed position. In the open position, the groove is exposed, and in the closed position, the groove is covered. The cover also includes a second groove that cooperates with the first groove when the cover is in the closed position to define a channel. The channel is configured to support the portion of the medical article received by the retainer on at least diametrically opposed sides thereof along the entire length of the received portion of the medical article. At least one retention member projects into the channel and is arranged to engage a portion of the medical article to inhibit longitudinal movement of the medical article through the channel. Interengaging structure also cooperates between the base and cover to releasably secure the cover to the base.

In accordance with an additional aspect of the present invention, the anchoring system comprises an anchor pad with upper and lower surfaces. At least a portion of the lower surface is formed by an adhesive layer. A retainer is affixed to the upper surface of the anchor pad and comprises a base and a cover. The base has a first groove to receive at least a portion of the elongated medical article. The cover is pivotally coupled to the base and is moveable between an open position and a closed position. The cover also includes a second groove that cooperates with the first groove when the cover is in the closed position to define a channel. The channel is configured to accept a portion of the medical article received by the base. The base and cover include interengaging structure which releasably secures together the base and the cover in the closed position. At least one retention mechanism is positioned within the channel and includes at least first and second members that are arranged to cooperate with one another when the cover is closed to hold a structural portion of the medical article between the first and second members without substantially occluding the inner lumen of the medical article.

Further aspects, features and advantages of the present invention will become apparent from the detailed description of the preferred embodiment that follows.

BRIEF DESCRIPTION OF THE DRAWINGS

The above mentioned and other features of the invention will now be described with reference to the drawings of a preferred embodiment of the present anchoring system. The illustrated embodiment of the anchoring system is intended to illustrate, but not to limit the invention. The drawings contain the following figures:

FIG. 5b is an elevational view of a distal end of the retainer of FIG. 5a;

DETAILED DESCRIPTION OF A PREFERRED EMBODIMENT

Figure 1:
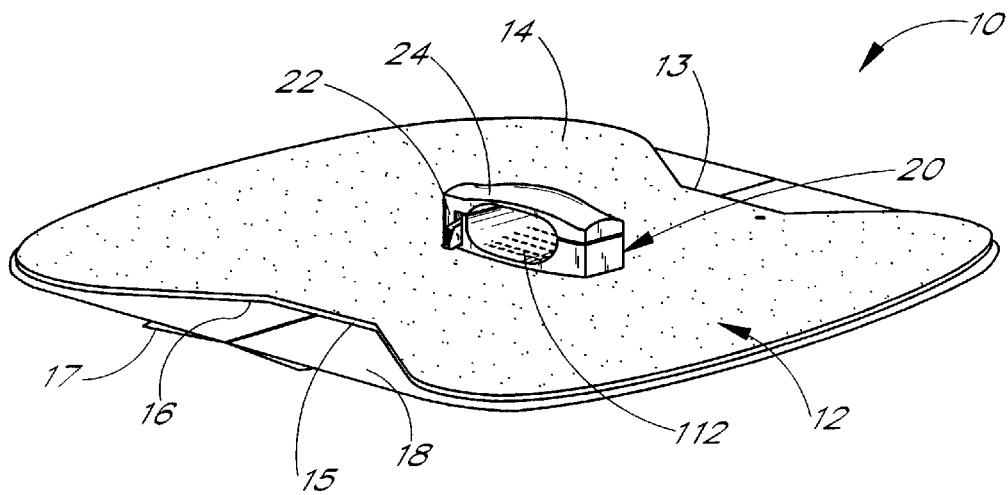
FIG. 1 is a perspective view of an anchoring system in accordance with a preferred embodiment of the present invention and illustrates the anchoring system from a proximal end.

The present embodiment of the medical article anchoring system is disclosed in the context of an exemplary Foley type catheter. The principles of the present invention, however, are not limited to Foley catheters. Instead, it will be understood by one of skill in this art, in light of the present disclosure, that the anchoring system and retainer disclosed herein also can be successfully utilized in connection with other types of medical articles, including other types of catheters, fluid drainage and delivery tubes and electrical wires. For example, but without limitation, the retainer disclosed herein can also be configured to receive and secure central venous catheters, peripherally inserted central catheters, hemodialysis catheters, surgical drainage tubes, feeding tubes, chest tubes, nasogastric tubes, scopes, as well as electrical wires or cables connected to external or implanted electronic devices or sensors. One skilled in the art may also find additional applications for the devices and systems disclosed herein. Thus, the illustration and description of the anchoring system in connection with a Foley catheter is merely exemplary of one possible application of the anchoring system.

The anchoring system described herein is especially adapted to arrest axial movement of the catheter with a slippery coating, as well as hold the catheter against the patient. For this purpose, the anchoring system 10 utilizes one or more retention mechanisms. The anchoring system accomplishes this though without meaningfully impairing (i.e., substantially occluding) the fluid flow through the catheter to a degree that would create complications. As described below, such retention mechanisms involve, among others, the shape of the channel that retains a section of the catheter, retaining structure either aligned with or positioned within the channel, a securement barb(s) or friction ridge(s) that bites into the catheter body without substantially occluding the catheter drainage lumen, and/or cooperating members that come together to clamp onto or pin a portion of the catheter (e.g., a webbing formed between the branches at the Foley catheter Y-site).

The anchoring system also desirably releasably engages the catheter. This allows the catheter to be disconnected from the anchoring system, and from the patient, for any of a variety of known purposes. For instance, the healthcare provider may want to remove the catheter from the anchoring system to ease disconnection of the catheter from the drainage tube or to clean the patient. The disengagement of the catheter from the anchoring system, however, can be accomplished without removing the anchoring system from the patient.

Before describing the present anchoring system in detail, a brief description of a Foley catheter is provided to assist the reader's understanding of the exemplary embodiment that follows. As best understood from FIG. 6, the catheter 8 includes a proximal tip with an inflatable balloon (not shown) and a distal end 110. The distal end 110 includes a Y-site 112 formed by an inflation branch 114 and a drainage branch 116. The drainage branch 116 and the inflation branch 114 merge together at the Y-site 112. The lumens of these branches assume either a coaxial or side-by-side arrangement on the proximal side of the Y-site 112 to form a main catheter body 118. On the distal side of the Y-site 112, a webbing 120 extends between the two branches 114, 116 at a point next to the Y-site 112.

Figure 2:
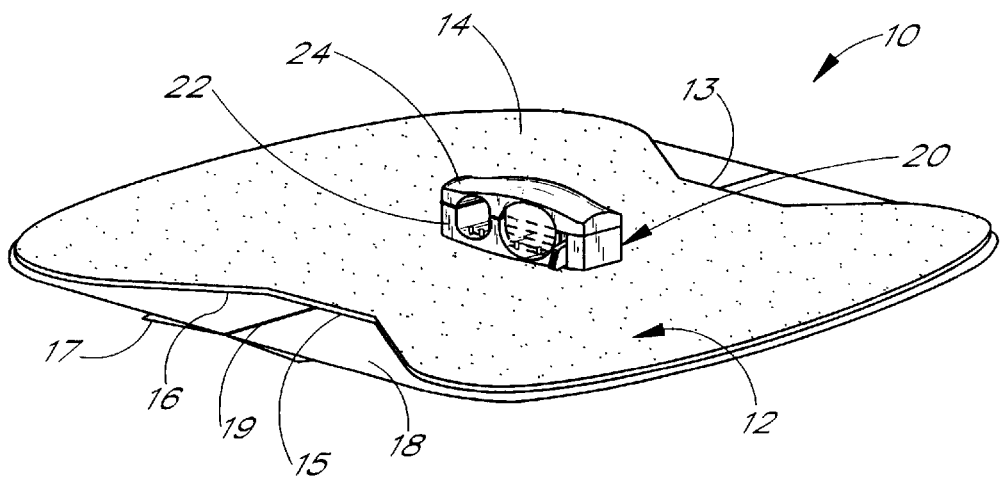
FIG. 2 is a perspective view of the anchoring system of FIG. 1 from a distal end.
Figure 3:
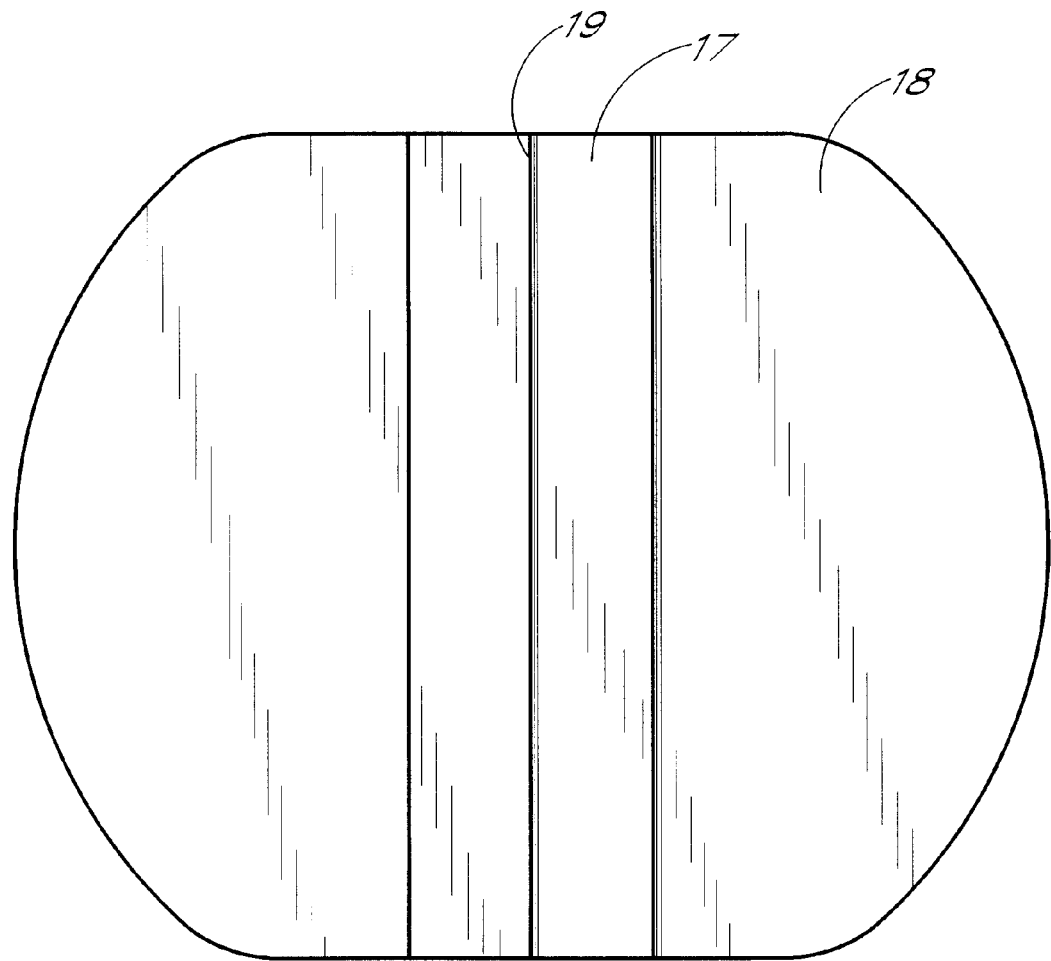
FIG. 3 is a bottom view of the anchoring system of FIG. 1.

With reference now to FIGS. 1 to 3, the anchoring system 10 includes an anchor pad 12 and a retainer 20. The anchor pad 12 secures the retainer 20 to a patient's skin. The anchor pad 12 has a lower adhesive surface 16 which adheres to the skin of a patient and a roughened upper surface 14 which supports a retainer 20. The retainer 20 is configured to accept and retain a section of a Foley catheter 8 within the anchoring system 10. In the illustrated embodiment, the retainer comprises a base 22 and a cover 24. The cover 24 is detachably secured to the base 22 and moveable between open and closed positions.

To assist in the description of these components of the anchoring system 10, the following coordinate terms are used. A "longitudinal axis" is generally parallel to the section of the catheter 8 retained by the anchoring system 10. A "lateral axis" is normal to the longitudinal axis and is generally parallel to the plane of the anchor pad 12. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. Also, the terms "proximal" and "distal", which are used to describe the present anchoring system 10, are used consistently with the description of the exemplary application. Thus, proximal and distal are used in reference to the center of the patient's body. A detailed description of the anchoring system 10, and its associated method of use, now follows.

FIGS. 1 to 3 illustrate an anchor pad 12 which desirably comprises a laminate structure with an upper foam layer (e.g., closed-cell polyethylene foam), and a lower adhesive layer. The lower adhesive layer constitutes the lower surface 16 of the anchor pad 12. The lower surface 16 desirably is a medical-grade adhesive and can be either diaphoretic or nondiaphoretic, depending upon the particular application. Such foam with an adhesive layer is available commercially from New Dimensions in Medicine of Columbus, Ohio. Although not illustrated, it will be understood that the anchor pad 12 can include suture holes in addition to the adhesive layer to further secure the anchor pad 12 to the patient's skin.

A surface of the upper foam layer constitutes an upper surface 14 of the anchor pad 12. The upper surface 14 desirably is roughened by corona-treating the foam with a low electric charge. The roughened or porous upper surface 14 improves the quality of the adhesive joint (which is described below) between the base 22 and the anchor pad 12. In the alternative, the flexible anchor pad 12 can comprise a medical-grade adhesive lower layer, an inner foam layer and an upper paper or other woven or nonwoven cloth layer.

A removable paper or plastic release liner 18 desirably covers the adhesive lower surface 16 before use. The liner 18 preferably resists tearing and desirably is divided into a plurality of pieces to ease attachment of the pad to a patient's skin. In the illustrated embodiment, the liner 18 is split along a center line 19 of the flexible anchor pad 12 in order to expose only half of the adhesive lower surface 16 at one time.

The liner 18 length, as measured in the lateral direction, extends beyond the center line 19 of the anchor pad 12 and is folded over, or back onto the liner 18. This folded over portion defines a pull tab 17 to facilitate removal of the liner 18 from the adhesive lower surface 16. A medical attendant uses the pull tab 17 by grasping and pulling on it so that the liner 18 is separated from the lower surface 16. The pull tab 17 overcomes any requirement that the medical attendant pick at a corner edge or other segment of the liner 18 in order to separate the liner 18 from the adhesive layer. The pull tab 17 of course can be designed in a variety of configurations. For example, the pull tab 17 can need not be located along a center line 19 of the anchor pad 12; rather, the pull tab 17 may be located along any line of the anchor pad 12 in order to ease the application of the anchor pad 12 onto the patient's skin at a specific site. For example, an area of a patient's skin with an abrupt bend, such as at a joint, may require that the pull tab 17 be aligned toward one of the lateral ends of the anchor pad 12 rather than along the center line 19.

In the illustrated embodiment, the anchor pad 12 also desirably includes a pair of opposing concave sections 13, 15 that narrows the center of the anchor pad 12 proximate to the base 22. As a result, the lateral sides of the anchor pad 12 have more contact area which provides greater stability and adhesion to a patient's skin.

With reference now to FIGS. 4–10, the retainer 20 includes a rigid structure principally formed by the base 22 and the cover 24. In the illustrated embodiment, the base 22 and cover 24 are integrally formed to comprise a unitary retainer 20. This can be accomplished in any of a variety of ways well known to those skilled in the art. For instance, the entire retainer 20 can be injection molded in order to reduce fabrication costs.

Additionally, as will be apparent from the below description, several features of the retainer (e.g., a latch keeper and a hinge) desirably are flexible. Suitable ridged but flexible materials include, for example, but without limitation, plastics, polymers or composites such as polypropylene, polyethylene, polycarbonate, polyvinylchloride, acrylonitrile butadiene styrene, nylon, olefin, acrylic, polyester, as well as moldable silicon, thermoplastic urethane, thermoplastic elastomers, thermoset plastics and the like. The illustrated retainer 20 preferably is formed by injection molded using polyethylene or polypropylene material. However, other materials can be utilized, and the retainer 20 can comprise a non-unitary base 22 and cover 24.

Figure 4:
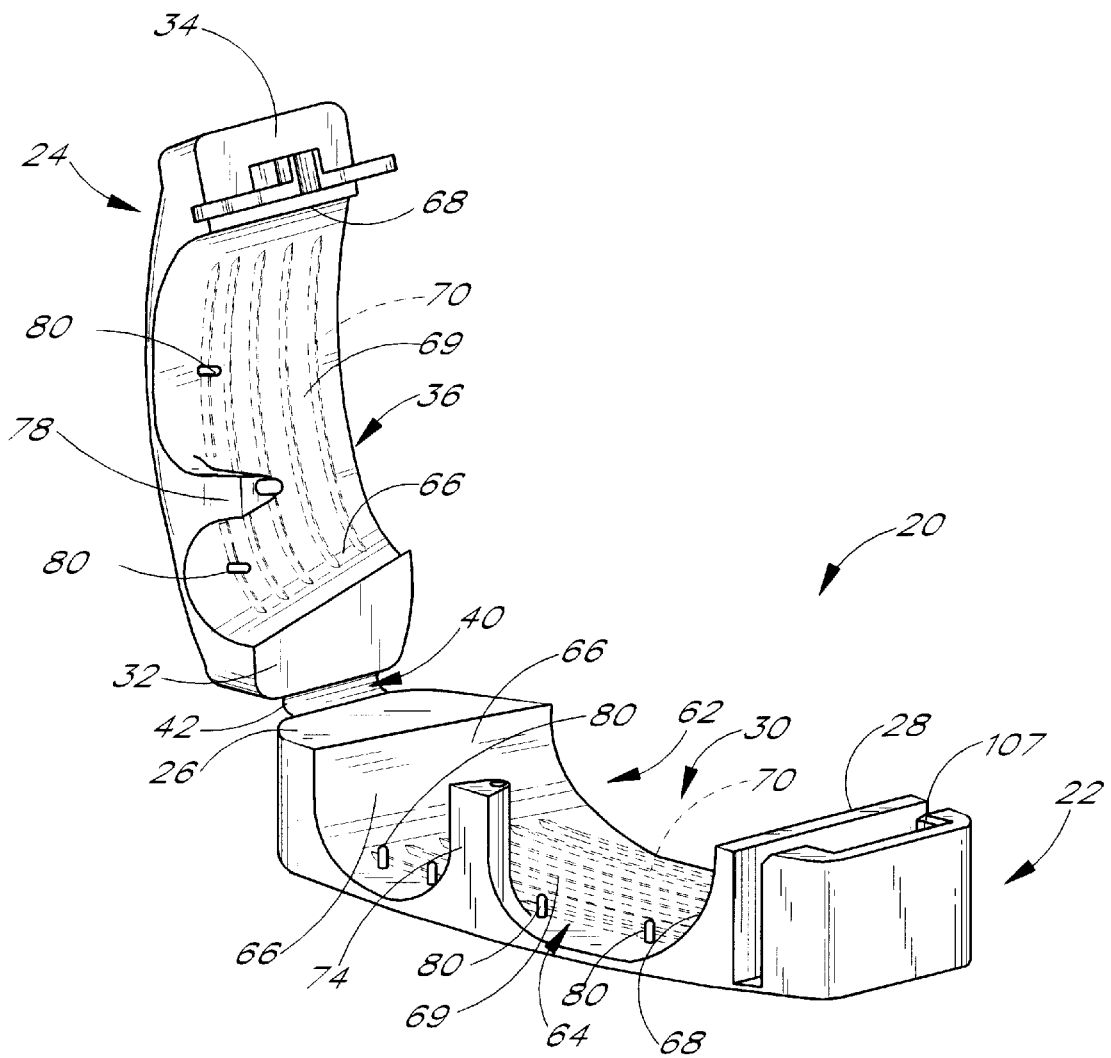
FIG. 4 is an elongated perspective view of a retainer of the anchoring system of FIG. 2 with a cover of the retainer in an open position.

With reference to FIG. 4, a base 22 in the illustrated embodiment comprises an elongated body of a generally parallelepiped shape. The base 22, however, can be configured in a wide variety of shapes as well, such as circular, square, triangular or the like in order to suit a particular application. The longitudinal dimension of the base 22 though desirably is sufficiently long to provide stability to the catheter 8 along its length. That is, the longitudinal length of the retained catheter portion is sufficient to inhibit rocking of the catheter 8 relative to the retainer 20 (i.e., to prevent the retainer 20 from acting as a fulcrum for the catheter). Also, the lateral dimension of the base 22 desirably allows the healthcare provider to easily and naturally grip the base 22, as well as provides space on which to locate a hinge 40 and a portion of the latch mechanism 80.

The base 22 includes first and second sides 26, 28. The first side 26 lies generally at one lateral end of the base 22, and the second side 28 lies at an opposite lateral end of the base 22.

Figure 6:
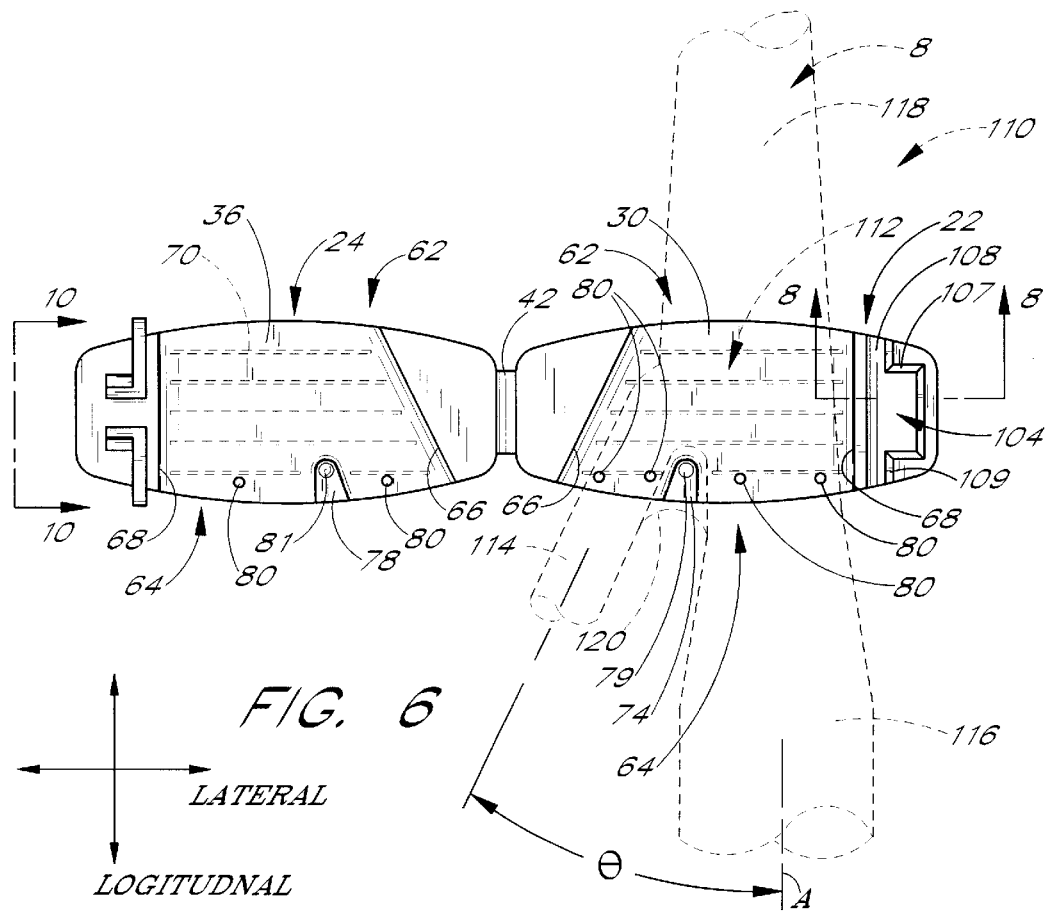
FIG. 6 is a top plan view of the retainer of FIG. 4 with the cover in a fully open position.

A groove 30 is formed on the base 22 between the first side 26 and the second side 28. In the illustrated embodiment, the groove 30 has generally a curvilinear cross-sectional shape. As best seen in FIG. 6, the lower groove 30 is also varied in width (i.e., in the lateral direction) along its longitudinal length. That is, the side walls of the lower groove 30 diverge from each other in a generally linear manner from one longitudinal side of the retainer 20 to the other longitudinal side of the retainer.

The base 22 of the retainer 20 is attached to the upper surface 14 of the anchor pad 12. The base 22 desirably is secured to the upper surface 14 by a solvent bond adhesive, such as cyanoacrylate or other bonding material. One such adhesive is available commercially as Part No. 4693 from the Minnesota Mining and Manufacturing Company (3M).

As also seen in FIG. 4, the cover 24 has an elongate shape which desirably is coextensive with the planar size and shape of the base 22 (i.e., desirably has the same geometric shape and size as the base 22); however, the cover 24 need not be the same size or shape as the base 22. For instance, the cover 24 can be sized to extend beyond any of the lateral, traverse, or longitudinal edge of the base 22 or, alternatively, can be sized so as to not extend to the lateral, traverse, or longitudinal edge of the base 22. The cover can also include a skirt or flange that extends over and/or about the base 22 or any portion thereof.

The cover 24 though desirably has a sufficient size to cover the lower groove 30 in the base and to accommodate a portion of the latch mechanism 80 and the hinge 40 which operate between the base 22 and the cover 24, as described below. The cover 24 also desirably is of a dimension which provides for easy manipulation. For example, the cover's size easily accommodates the grasp of a medical attendant.

The cover 24 includes a first side 32 which lies generally at one lateral end of the cover 24. The first side 32 of the cover therefore generally corresponds to the first side 26 of the base 22. The cover 24 also has a second side 34. The second side 34 lies generally toward a lateral end of the cover 24, opposite of the first end, and corresponds generally to the second side 28 of the base 22.

An upper groove 36 is formed on an inner catheter of the cover 24 between the first and second sides 32, 34 of the cover 24 and corresponds generally to the lower groove 30 formed in the base 22. The width of the upper groove 36 is also varied in the lateral direction along its longitudinal length. That is, the side walls of the upper groove 36 diverge from each other in a generally linear manner from one longitudinal end of the cover 24 to the other longitudinal end.

The cover 24 is flexibly coupled to the base 22 by way of a flexible coupling or hinge 40. The coupling 40 desirably comprises a flexible band 42 that can take any number of forms to mechanically connect the cover 24 to the base 22 while permitting pivotal movement of the cover 24 relative to the base 22 so as to enable engagement or disengagement of these parts, as described below. In the illustrated embodiment, the band 42 is formed of flexible material, desirably of the same material from which the base 22 and cover 24 are comprised. Advantageously, the hinge 40 is integrally molded with the base 22 and the cover 24 to form a unitary member, as noted above. The hinge 40 is located at an outer edge of the base 22 and the cover 24; however, the hinge 40 need not be laterally located at an extreme end of the base 22 or cover 24.

As best understood from FIG. 6, the width of the hinge 40, as measured in the longitudinal direction, is desirably less than that of either the base 22 or the cover 24 to allow some leeway or play when engaging or disengaging the cover 24 to the base 22. That is, this shape allows the hinge 40 to twist to some degree to compensate for some manufacturing tolerances; however, the hinge 40 can have at least as large of a longitudinal dimension as the base 22 and the cover 24.

The hinge 40 is desirably integrally formed along a common corresponding exterior surface of the cover 24 and base 22. In the illustrated embodiment, as best understood from FIG. 5b, the hinge 40 has generally a U-shape when the cover 24 is closed, and extends from both the base 22 and the cover 24 in the lateral direction to the side of the retainer 20. A gap 44, corresponding to a transverse height of the hinge 40, exists between the base 22 and cover 24. This gap 44, however, can be reduced or eliminated from the retainer for some applications by using a different hinge design.

Figure 5A:
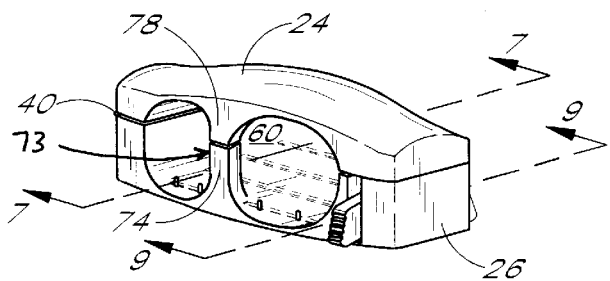
FIG. 5a is a perspective view of the retainer illustrated in FIG. 2 with the cover in a closed position.

The hinge 40 enables the cover 24 to move between the open position and the closed positions. The open position, as illustrated in FIG. 4, is characterized by exposing the grooves 30, 36 in the base 22 and the cover 24 in the transverse direction and thereby spacing apart the base 22 and the cover 24. When in the open position, the retainer 20 is capable of receiving a portion (e.g., the Y-site 112) of the Foley catheter 8. The closed position, as illustrated in FIG. 5a, is characterized by the cover 24 lying in contact or near contact with the base 22 so as to position the upper groove 36 above the lower groove 30. When in the closed position, the retainer 20 surrounds the received portion of the catheter.

Figure 5B:
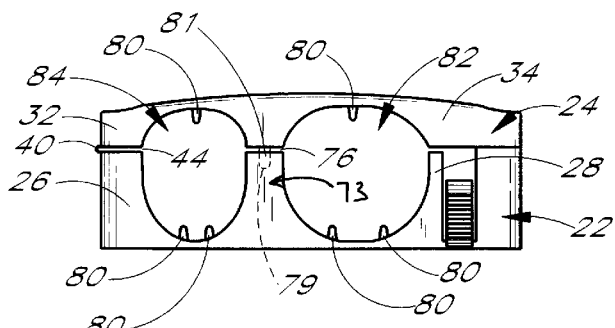

The hinge 40 need not provide 180° of movement of the cover 24 relative to the base 22 to establish the closed position and a fully open position, as illustrated by FIGS. 5b and 6. For instance, the hinge 40 can permit a smaller degree of movement (e.g., 90°) between the base 22 and the cover 24 while still providing enough space to transversely insert the catheter into the retainer 20.

The grooves 30, 36 formed in the base 22 and the cover 24 define a channel 60 when the retainer 20 is closed. The channel 60 is capable of receiving a portion or length of the catheter 8 and is generally configured to house, grip and secure the affected catheter portion. The channel 60 may have a variety of configurations, as discussed above in connection with the grooves 30, 36, in order to accommodate a particular medical article. In the illustrated embodiment, the channel 60 generally has circular cross-sectional shape at its proximal end 62 and a generally oblong cross-sectional shape at its distal end 64 (although, in the illustrated embodiment, the distal end 64 is divided by a pair of cooperating post, which will be described below). The channel smoothly tapers in cross-sectional size from its smaller proximal end 62 to its larger distal end 64. The channel 60 consequently generally has a truncated V-shape, as best understood by inspecting the shapes of the grooves 30, 36 in FIG. 6.

Although the channel 60 may take the form of various shapes depending upon its application (i.e., depending upon a shape of the retained portion of the medical article for which the retainer is designed to be used), the channel 60 does have a sufficient length in the longitudinal direction to stabilize the catheter, rather than act as a fulcrum for the catheter, as mentioned above. That is, the retainer receives a sufficient length of the catheter to inhibit movement of the catheter in the lateral, longitudinal and transverse direction (i.e., to inhibit yaw, pitch and axial movement of the catheter), without kinking the catheter.

When the cover 24 is closed, a section of the catheter 8 is captured within the retainer 20. Thus, the retainer 20 at least restricts, if not prevents, lateral and transverse movement of the retained section of the catheter 8.

Inhibiting movement of the catheter 8 in the longitudinal direction when the catheter 8 is secured within the channel 60 is desirably accomplished by one or more retention mechanisms that associate with the channel 60. With reference to FIGS. 4, 5 and 6, one such retention mechanism involves the shape of the channel 60 itself. The interaction between the truncated V-shape of the channel 60 and a corresponding shape of the catheter Y-site 112 inhibits proximal longitudinal movement.

As best understood from FIG. 6, the proximal end 62 of the channel 60 is sized to receive only the main body 118 of the catheter 8. The distal end 64 of the channel 60 is sized to receive both branches 114, 116 (i.e., the inflation lumen section and the drainage lumen section) at the distal side of the Y-site 112. And between its distal and proximal ends 64, 62, the channel 60 is configured to receive the catheter Y-site 112. In the illustrated embodiment, a second side 68 of the channel 60 (formed by the second sides 28, 34 of the base 22 and the cover 24) lies generally parallel to a longitudinal axis of the portions of the catheter drainage lumen received by the channel 60; however, a first side 66 of the channel 60 (formed by the first sides 26, 32 of the base 22 and cover 24) is angled relative to the second side 68. The first side 66 of the channel 60 desirably varies in a tapering or linear manner. An angle of divergence between the first and second sides 66, 68 of the channel 60 desirably is between about 10° and about 70°, and more preferably is between about 30° and about 45°, and generally matches an angle of intersect θ between the two branches 114, 116 of the catheter 8.

Because the catheter Y-site 112 is large in cross-section than its main body 118, the Y-site 112 usually cannot be pulled proximally through the smaller proximal end 62 of the retainer channel 60. The shape of the channel 60 thus inhibits longitudinal movement of the catheter in the proximal direction.

Variations on the channel's shape of course are also possible, as noted above. For instance, the second side 68 of the channel 60 can vary from the first side 66 in a curvilinear manner and/or can include a gouge, protrusion or similar geometric abnormality so as to cooperate with a corresponding portion of the received catheter length. Also, there is no requirement that only the first side 66 vary relative to an axis A of the received catheter length. Either the first 66 or second 68 side, or both sides, may vary in distance relative to the axis A of the received catheter length so as to inhibit longitudinal movement of the retained section of the catheter 8. The channel, however, can have a straight or uniform cross-sectional shape where the retainer includes at least another mode of the retention mechanism.

The interaction between the surface 69 of the retainer channel 60 and the catheter Y-site 112 also creates friction to inhibit longitudinal movement through the channel 60. The degree of interference between the catheter 8 and the retainer 20, however, cannot be so great as to significantly occlude the catheter 8.

Another retention mechanism to inhibit axial movement of the catheter 8 involves one or more friction ridges 70 located on the channel surface 69. In the illustrated embodiment, depicted by FIGS. 4 and 9, the ridges 70 are integrally formed with the base 22 and the cover 24 and project into the channel 60. Because the illustrated embodiment also includes securement barbs, which will be described below, the friction ridges 70 are illustrated in phantom to convey that the ridges 70 can be used together with or in the alternative to the securement barbs.

The ridges 70 are desirably of smooth solid construction; however, they may be of hollow construction. The ridges in the illustrated embodiment have generally triangular cross-sectional shapes and angle toward one end of the channel 60. The ridges 70, however, can have other cross-sectional shapes which would interfere with axial movement of the catheter 8 through the channel 60.

Figure 9:
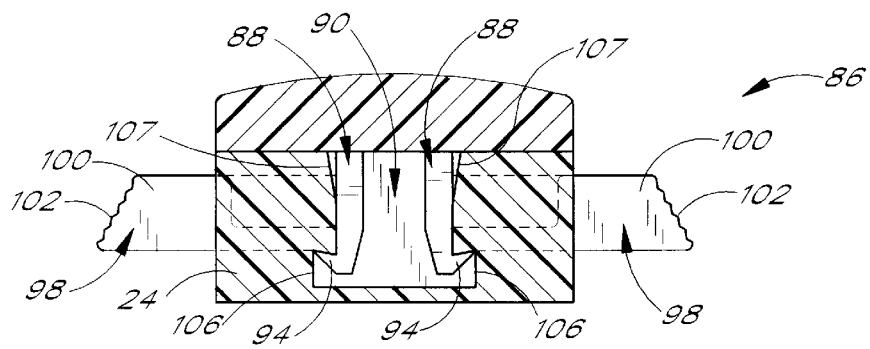
FIG. 9 is a cross-sectional view of the retainer of FIG. 5a, taken along the line 9—9.

In the illustrated embodiment, as best seen in FIG. 9, each of the ridges 70 desirably has a front wall or leading edge 72 that forms an angle of less than 90 degrees as measured between the front wall 72 and the channel surface 69. The ridges 70 slightly protrude into the channel 60, desirably at a transverse distance of between 0.1 to 10 mm for the given application. As best seen in FIG. 6, the ridges 70 also lie generally normal to a longitudinal axis through the channel 60.

When so arranged, the friction ridges 70 gently, but securely bite or press into an outer surface of the catheter Y-site 112. Such contact does not occlude or otherwise meaningfully impair fluid flow in the catheter lumens because of the compliant nature of the catheter body material and because of the degree to which the ridges bite into the catheter body. This degree of contact, however, coupled with the angular orientation of the ridges inhibits movement of the catheter 8, especially in a direction opposite of that in which the ridges are angled.

A retaining structure 73, which protrudes into the channel 60, may also be used to inhibit axial movement of the catheter. The retaining structure 73 forms an upstanding member transversely positioned relative to the anchor pad 12. The retaining structure 73 is arranged to lie between the branches at the catheter Y-site 112 retained by the retainer 20 so as to inhibit axial movement of the catheter 60 in the distal direction. Thus, the combination of the tapering channel shape and the retaining structure 73 inhibits axial movement of the retained section of the catheter 8 in both the proximal and distal directions.

The retaining structure 73 desirably has a sufficient height to inhibit axial movement of the catheter 8 in the distal direction. For this purpose, the retaining structure 73 has a height, in the transverse direction, of at least about 25% of the height of the channel 60 at the location at which the structure is positioned. In the present application, the retaining structure desirably extends across channel 60.

In the illustrated embodiment, the retaining structure 73 is formed by a base post 74 and a cover post 78. The base post 74 desirably is integrally formed with the base 22, and is located in the channel 60 toward the distal end 64 of the channel 60. The cover post 78 is integrally formed with the cover 24 also at the distal end 64 of the channel 60. Although in the illustrated embodiment, the base post 74 and cover post 78 lie within the channel 60, the posts 74, 78 can be located outside the distal end 64 of the channel 60.

In one mode, the base post 74 is sized to extend to a position where its upper end lies near or contacts the webbing 120 of the catheter 8 that extends between the Y-site branches 114, 116. In the illustrated embodiment, the upper end of the post 74 lies generally even with the upper surface of the first and second sides 26, 28 of the base 20, as best seen in FIG. 4. The cover post 78 similarly extends to a point which is generally flush with a plane defined by the inner surfaces of the cover first and second sides 32, 34 that lie adjacent to the base 22.

As best seen in FIG. 6, the lateral position of the post 74 within the channel 60 corresponds with the merge point between the inflation lumen branch 114 and the discharge lumen branch 116 of the Foley catheter 8. The post 74 divides the channel 60 at the channel's distal end 64.

The cover post 78 is configured and arranged on the cover 24 in a manner similar to that described above in connection with the post 74 on the base 22. The post 78 thus generally opposes the base post 74. By this particular design, as understood from FIG. 6, the combination of the posts 74, 78 and the channel 60 define a generally Y-shaped recess between the channel's proximal and distal ends 62, 64.

In the illustrated embodiment, the transverse height of the cover post 78 is less than that of the base post 74. The posts 74, 78, however, can have equal heights or the cover post 78 can be longer than the base post 74. Together though, as best seen in FIG. 5b, the posts 74, 78 desirably span the channel 60 in the transverse direction, except for a small gap 76 formed at their interface. This gap 76 can be slightly less than a thickness of the catheter webbing 120 between the Y-site branches 114, 116, for the reasons described below, and corresponds to the gap 44 provided by the hinge 40 when the cover 24 is closed.

The posts 74, 78 thus extend between these two branches 114, 116 of the catheter 8 when the catheter Y-site 112 is positioned within the channel 60. Together the posts 74, 78 acts as a stop against longitudinal movement of the catheter 8 in the distal direction. That is, longitudinal movement in the distal direction causes the catheter Y-site 112 to contact the posts 74, 78. The posts 74, 78, being of rigid construction, prevent further longitudinal movement.

Although the posts 74, 78 can have a variety of cross-sectional shapes, the posts 74, 78 desirably have a generally triangular cross-sectional shape in the present application so as to correspond to the space between the two catheter branches 114, 116 at the Y-site 112. The proximal edge of the posts, however, advantageously is rounded to eliminate sharp contact between the catheter 8 and the retainer 20 at this location.

The posts 74, 78 can also include interengaging elements to interlock the posts 74, 78 in the transverse direction and prevent the catheter 8 from being pulled through the gap 76 between their ends. In the illustrated embodiment, a pin or projection 81 and a corresponding receptacle 79 are arranged between the interfacing ends of the posts 74, 78. As best seen in FIGS. 4, 5b and 6, the receptacle 79 is formed at the transverse end of the base post 74, extending into the post 74 in a transverse direction from an interface surface of the post 74. The projection 81 extends from an end of the cover post 78 in a direction parallel to a transverse axis of the post 78. The projection 81 is configured to fit within the receptacle 79. When the cover 24 is closed, the pin 81 extends into the receptacle 79 to interlock together the posts 74, 78.

Another possible retention mechanism to inhibit axial movement of the catheter 8 relative to the retainer 20 involves protuberances that are arranged to cooperate with one another when the cover 24 is closed. For instance, in one mode, the cooperating posts 74, 78 can be arranged to capture a structural portion of the catheter (e.g., the catheter webbing 120) between them without substantially occluding an inner lumen of the catheter 8, as schematically represented in FIG. 6. In another mode, the projection 81 can be employed without the receptacle 79 to simply pin a portion of the catheter (e.g., its webbing) against a surface of the retainer 20. For instance, the projection 81 can extend from a portion of either the base 22 or the cover 24 and cooperate with a corresponding surface (be it a post, platform or channel surface) that opposes the projection 81 when the cover is closed. The projection 81 would protrude into the portion of the catheter and pin it against the corresponding surface.

Alternatively, the projection 81 can be used with the receptacle 79 to capture a section of the catheter. When the cover 24 is closed, the projection 81 could force a portion of the catheter body 8 into the receptacle 79 to capture a structural portion of the catheter 8 between these components without occluding an inner lumen of the catheter. This engagement of the retainer 20 with the catheter body 8 would inhibit axial catheter movement relative to the retainer 20.

One or more securement barbs 80 can also be used to retain the catheter in the longitudinal direction. In the illustrated embodiment, each barb 80 has a generally conical shape with a blunt tip. The barb 80, in the present application, desirably extends into the channel 60 by an amount ranging between about 0.1 mm and about 3 mm.

The retainer desirably includes at least one set of securement barbs 80, indicated collectively by reference numeral 82, which are arranged within the channel 60 to cooperate with one another. The barbs 80 advantageously are arranged within the same general lateral plane (i.e., a plane defined by the lateral and transverse axes), and are spaced apart from one another. In addition, the barbs 80 desirably are spaced on generally opposite surfaces 69 of the channel 60 in a staggered arrangement. That is, the position of the barbs 80 alternate between the cover surface and the base surface in the lateral direction. The resulting overlapping pattern of the barbs 80 securely holds the catheter 8 without imparting torque to the catheter 8 if pulled in a longitudinal direction. In the illustrated embodiment, one barb 80 is positioned on the cover surface and is generally equally distanced in the lateral direction from the adjacent side of the channel 60 and the adjacent side of the post 78. A pair of barbs 80 is positioned on the base surface. These barbs 80 are spaced apart from one another and the pair is symmetrically positioned relative to a transverse axis that extends through the barb 80 on the cover surface.

Figure 7:
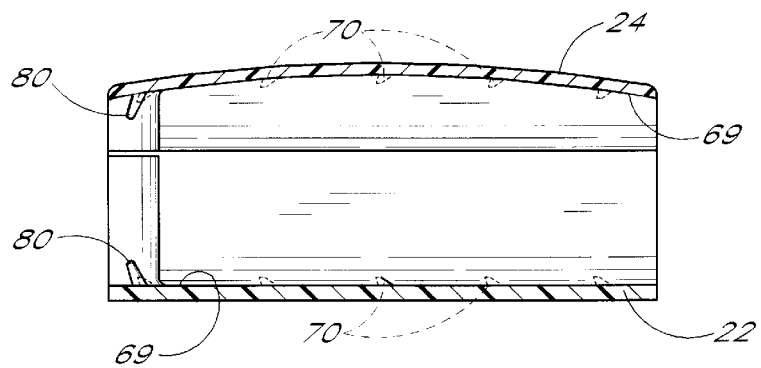
FIG. 7 is a cross-sectional view of the retainer of FIG. 5a, taken along the line 7—7.

The present retainer 20 also includes a second set of securement barbs, indicated collectively by reference numeral 84, which are arranged generally in accordance with the above description; however, fewer number of barbs, as well as fewer sets, can also be used. In the illustrated embodiment, one set of barbs 84 is placed between the posts 74, 78 and the first sides 26, 32 of the cover 24 and the base 22, and the other set of barbs 82 is placed between the posts 74, 78 and the second sides 28, 34 of the cover 24 and the base 22. As best seen in FIG. 7, the barbs 80 of the first set are desirably angled toward the distal end 64 of the channel 60 to inhibit movement of the catheter's inflation lumen branch 114 in the proximal direction when the catheter 8 is pulled proximally, as well as when the catheter 8 discharge branch 116 is pulled distally. The barbs of the second set 82, however, are desirably angled toward the proximal end 62 of the channel 60 to inhibit movement of the catheter 8 when the catheter's discharge branch 116 is pulled distally.

Figure 8:
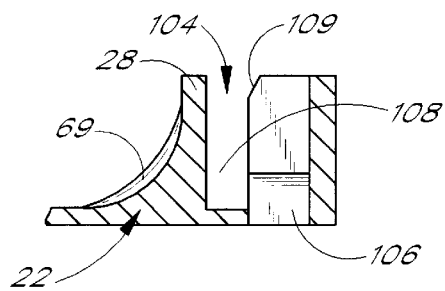
FIG. 8 is a cross-sectional view of a latch receptacle of the retainer illustrated in FIG. 6, taken along the line 8—8.
Figure 10:
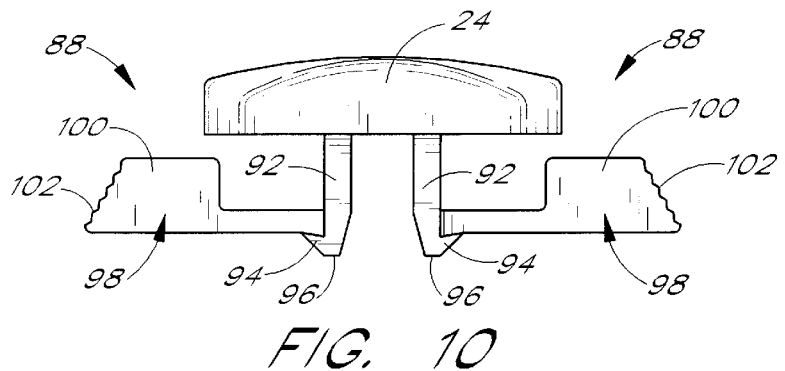
FIG. 10 is a partial side elevational view of the retainer of FIG. 6 as viewed in the direction of line 10—10, and illustrates the cover and an associated latch mechanism of the retainer.

To firmly hold the affected catheter portion within the channel, the base 24 and the cover 22 include interengaging structure to couple them together in the closed position. In the illustrated embodiment, as best seen in FIGS. 8–10, a latch mechanism 86 is used to secure the cover 24 to the base 22. The latch mechanism 86 comprises at least one moveable keeper 88 and at least one latch 90. The keeper 88 is arranged on the cover 24 while the latch 90 is arranged on the base 22; however, these components can be flip-flopped on the base and the cover.

As best seen in FIG. 10, each keeper 88 includes a bar 92 extending toward the base 22 from the second side 39 of the cover 24. A tang 94 is formed at a lower end 96 of the bar 92. Desirably, the lower end 96 of the bar 92 is relatively blunt and smooth to prevent it from puncturing the gloves or skin of a healthcare provider or catching on other materials. An operator lever 98 extends to the side of the bar 92 and includes an enlarged platform or ear 100 at its outer end. The platform 100 desirably include ridges or knurls, as seen in FIG. 10, on an inclined surface 102. The inclined surface 102 slopes outward in a direction toward the base 22 such that a component of a transverse force applied to the surface 102 will cause the bar 92 to deflect inward. The entire keeper 88 desirably is formed with the cover 24 to form a unitary piece.

The latch mechanism 86 includes a receptacle 104 that receives the bar 92 and the tang 94. The latch receptacle 104 includes an inner notch 106 into which the tang 94 snaps when the cover 24 is in the closed position; however, the tang can be arranged in the receptacle and the notch be positioned on the bar to accomplish the same effect. The latch 90 desirably is formed with the base 22 as a unitary piece.

In the illustrated embodiment, as best seen in FIG. 10, the cover includes two keepers 88 that are mirror-images of each other. And, as best seen in FIG. 7, the latch 90 includes two notches 106, each of which is arranged to receive one of the keeper tangs 94 when the cover 24 is closed.

An entrance of the receptacle 104 includes chamber edges 107. The chamfer edges 107 slope inward toward the center of the receptacle 104 to cause the keeper bars 92 to bend inward when inserting the keepers 88 into the latch receptacle 104.

As best understood from FIGS. 6, 8 and 9, the second side 28 of the base 22 also includes a slot 108 to receive a portion of the operator levers 98 and the bars 92 of the keepers 88 when the associated tangs 94 are inserted into the receptacle 104. The entrance to the slot 108 also includes a chamfer 109 on its outer edge to facilitate insertion of the keeper levers 98 into the slot 108.

In operation, the cover 24 can swing toward the closed position. The relatively thin strip of material forming the coupling allows the hinge 40 to bend when finger pressure is exerted on the cover 24 to close it. The lower ends 90 of the keeper bars 92 contact the chamfered edges 107 of the latch receptacle 104 when the cover 24 nears its closed position. Continued pressure forces the bars 92 inward (toward each other) to permit the tangs 94 to pass through a narrow section of the receptacle. The slot 108 of the receptacle 104 receives the operator levers 98 as the tangs 94 are pushed further into the receptacle 104. The tangs 94 snap into the notches 106, under the spring force provided by the deflected bars 92, when the cover 22 sits atop the base 24. The interaction between the tangs 94 and the corresponding surfaces of the notches 106 hold the cover 24 in this position.

As best seen in FIG. 9, the operator levers 98 extend to the longitudinal sides of the base 24 when the cover 24 is latched. The platforms 100 thus remain exposed.

A medical attendant presses downward on the platforms 100 to open the latch mechanism 80. A downwardly force applied to the angled outer surface 102 exerts an inward force component which deflect the corresponding bar 92 inward and release the tangs 94 from the notches 106. The inherent spring force stored in the bent hinge band 42 assists with providing a transverse force that moves keepers 88 out of the receptacle 104. The medical attendant can then open the cover 24 and expose the inner grooves 30, 36 of the base 22 and the cover 24.

The releasable engagement between the cover 24 and the base 22 allows the same retainer 20 to be used for an extended period of time, while permitting repeated attachment and reattachment of the catheter to the anchoring system 10. In addition, the hinged connection connecting the cover 24 to the base 22 ensures that the cover 24 will not be lost or misplaced when the catheter is detached from the anchoring system 10. The medical attendant wastes no time in searching for a cover, nor in orienting the cover prior to latching.

Figure 11:
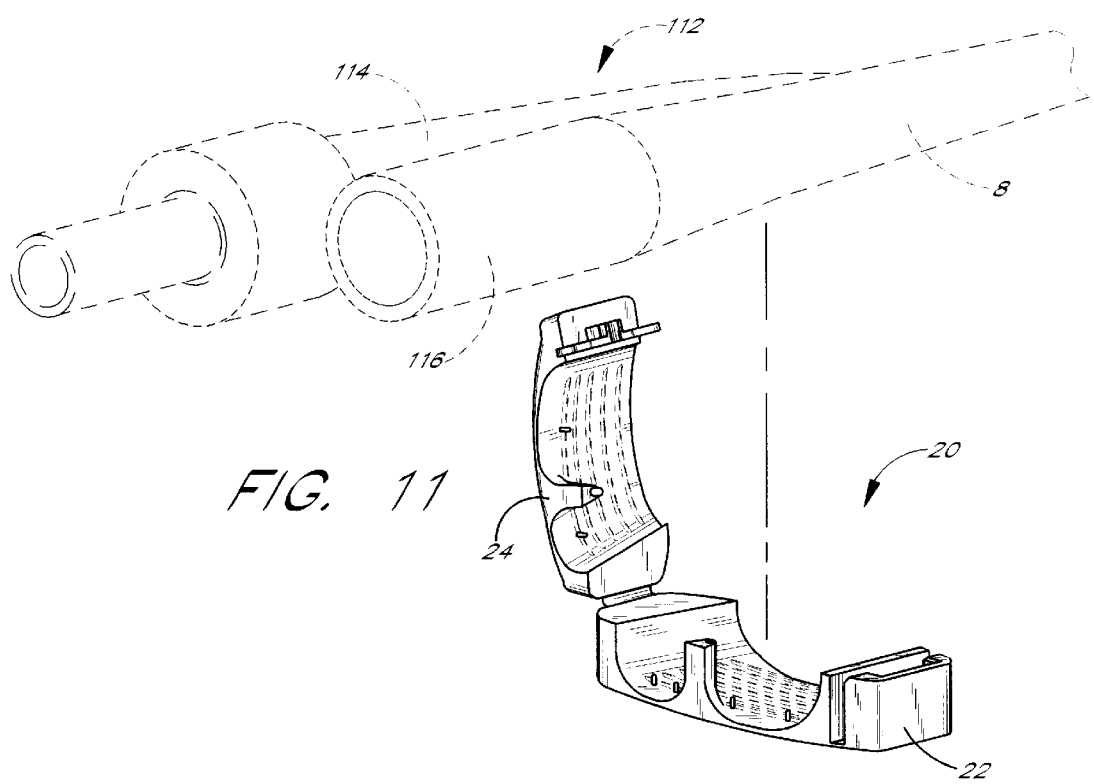
FIG. 11 is a perspective view of the anchoring system of FIG. 1, and illustrates the cover in an open position and a catheter aligned above the anchoring system for insertion therein.
Figure 12:
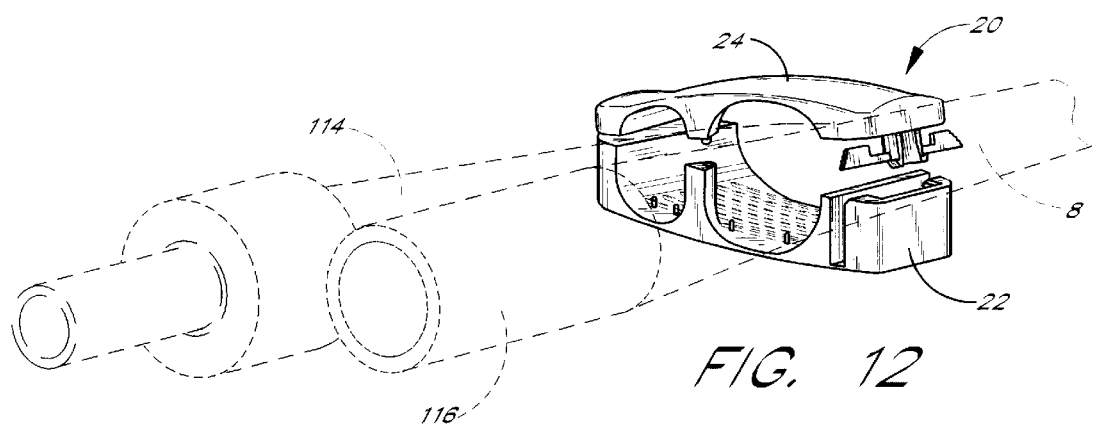
FIG. 12 is a perspective view of the anchoring system of FIG. 1, and illustrates the cover in a partially closed position with a channel formed by the cover and base of the anchoring system receiving the catheter.
Figure 13:
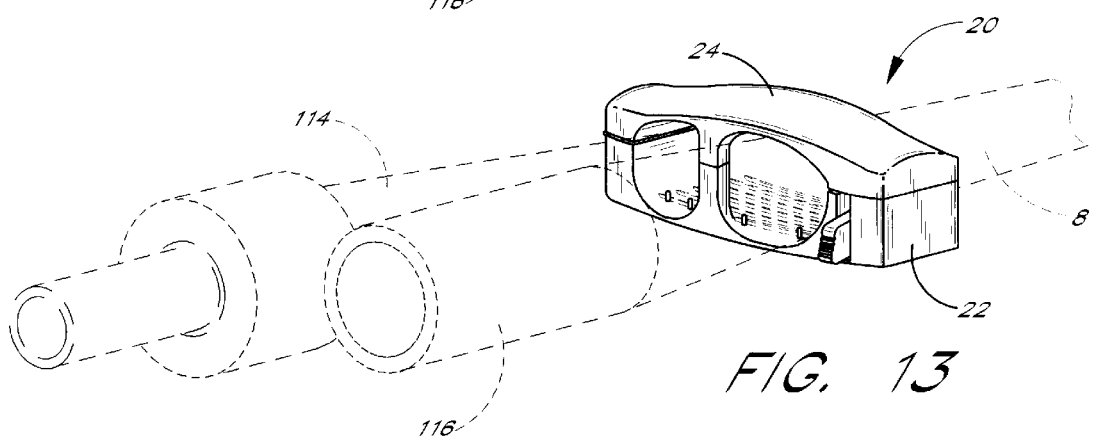
FIG. 13 is a perspective view of the anchoring system of FIG. 1, and illustrates the cover in a closed position with the catheter secured within the channel of the anchoring system.

As illustrated in FIGS. 11–13, a medical attendant may secure a Foley catheter (or other medical article) to a patient using the above-described anchoring system (or a readily apparent modification thereof). The medical attendant first opens the retainer 20 to expose the groove 30 on the base 22. Once opened, a catheter 8 may be transversely aligned over the groove 30. The catheter 8 may then be placed into the channel 60. If the channel 60 is formed with a post 74 (or another protuberance) for use with a Y-site, the first and second branches 114, 116 are aligned around the post 74 and the catheter Y-site 112 is aligned to securely fit within the remaining groove confines. Once the catheter 8 is so aligned and placed into the groove 30, the cover 24 is closed and latched, in the manner described above. The shapes of the grooves 30, 36 ensure that the channel supports the catheter Y-site 112 on at least diametrically opposed sides thereof along the entire retained length of the catheter Y-site. This not only enhances frictional contact between the retainer 20 and the catheter 8, but it also prevents the catheter 8 from kinking or crimping with the retainer 20 and thereby occluding one or more of the catheter lumens.

In the illustrated embodiment, the posts 74, 78 come together with the projection 81 inserting into the receptacle 79 when the cover is closed. The posts 74, 78 therefore are interlocked in this position to form a stop on the distal side of the Y-site 112 that spans entirely across the channel's transverse length. The securement barbs 80 also bite into the body of the catheter Y-site 112 to resist movement of the catheter branches 114, 116 in a direction opposite of the direction in which they are angled.

If the catheter 8 is pulled in the proximal direction, the tapered shape of the channel 60 prevents the larger distal end of the Y-site 112 from pulling through the retainer. The second set of securement barbs 84, which bite into the inflation lumen branch 114, also inhibit movement of the catheter in this direction. And if the retainer employ posts or projections that clamp onto or pin the catheter webbing within the channel, then this engagement between the retainer and the catheter would further secure the catheter in place.

If the catheter discharge branch 116 is pulled in the distal direction, the interlocked posts 74, 78 inhibit this movement. The first set of securement barbs 82 bite into the discharge branch 116 and also oppose movement of the catheter branch 116 in this direction. A distal pulling force on the discharge branch 116 also tends to pull the inflation lumen branch 114 around the posts 74, 78. The second set of securement barbs 84 also inhibits this reaction to further anchor the catheter Y-site 112 within the retainer 20.

The retainer 20 thus inhibits longitudinal movement of the catheter 8 relative to the retainer, even when used with a lubricated catheter. The holding effect provided by each of the retention mechanisms, however, does not substantially occlude the lumens of the catheter. The interaction of the protuberances (i.e., the posts and/or projection) only affects the catheter webbing 120 (or like structure) and does not bear against the catheter body. Likewise, the interaction between the shape of the channel and posts restricts movement of the catheter in both axial directions, but does not crimp or kink the catheter body when it is inserted within the channel and about the posts. And although the securement barbs bear against the catheter body, their limited bite does not significantly occlude the corresponding catheter lumen.

The illustration of the retainer as including all of the above-described forms of the retention mechanisms is merely exemplary. The retainer can include only one retention member or possibly several; it need not include all. In addition, any combination of the retention members in the retainer is also possible.

The present anchoring system thus provides a sterile, tight-gripping, needle and tape-free way to anchor a medical article to a patient. The retainer thus eliminates use of tape, and if prior protocol required suturing, it also eliminates accidental needle sticks, suture-wound-site infections and scarring. In addition, the retainer can be configured to be used with any of a wide variety of catheters, tubes, wires, and other medical articles. Patient comfort is also enhanced and application time is decreased with the use of the present anchoring system.

Although this invention has been described in terms of a certain preferred embodiment and suggested possible modifications thereto, other embodiments and modifications apparent to those of ordinary skill in the art are also within the scope of this invention. Accordingly, the scope of the invention is intended to be defined only by the claims which follow.

What is claimed is:

1. An anchoring system for securing an elongated medical article to a patient, comprising:
    an anchor pad having an upper surface and a lower surface, the lower surface including an adhesive layer on at least a portion of the surface; and
    a retainer mounted on the upper surface of the anchor pad and capable of receiving a portion of the medical article, the retainer including:
        a base having first and second sides, and a groove with a generally curvilinear cross-sectional shape;
        a cover having a first side and a second side, the first side of the cover being attached to the first side of the base, and the second side of the cover being moveable between a closed position, in which the second side of the cover lies generally above the second side of the base, and an open position, in which the second side of the cover is spaced apart from the second side of the base so as to expose the groove in the base, the cover including a groove having a generally curvilinear cross-sectional shape corresponding in position to the groove in the base to define a channel when the cover lies in the closed position, the defined channel having a curvilinear cross-sectional shape with a cross-sectional area of the channel varying along the length of the channel; and
        a latching mechanism operable between the base and the cover to releasably secure the second side of the cover to the second side of the base.

2. An anchoring system as in claim 1 additionally comprising at least one securement barb that is arranged on at least a portion of one of the curvilinear surfaces of the groves on the base and the cover.

3. An anchoring system as in claim 2, wherein the securement barb is angled toward one end of the channel.

4. An anchoring system as in claim 2 additionally comprising a plurality of securement barbs, and at least a portion of the securement barbs being arranged on opposing groove surfaces of the base and the cover in a generally staggered manner.

5. An anchoring system as in claim 4, wherein a least a portion of the securement barbs are angled toward one end of the channel and another portion of the securement barbs are angled toward the other end of the channel.

6. An anchoring system as in claim 4, wherein at least a first securement barb of the plurality of barbs extends from the base groove surface and at least a second securement barb of the plurality of barbs extends from the cover groove surface, and the first and second securement barbs are arranged generally within the same plane that extends generally normal to a longitudinal axis of the channel.

7. An anchoring system as in claim 1 additionally a plurality of friction ridges being located at least over a portion of one of the curvilinear surfaces of the grooves on the base and cover.

8. An anchoring system as in claim 7, wherein the friction ridges are angled toward one end of the channel.

9. An anchoring system as in claim 1 additionally comprising a post which is located at least near the channel and extends generally normal to a longitudinal axis of the channel.

10. An anchoring system as in claim 9 additionally comprising another post arranged to oppose the first post with one of the posts located on the cover and the other post located on the base.

11. An anchoring system as in claim 10, wherein one of the posts includes at least one projection that protrudes toward the other post, and the other post includes at least one receptacle that receives at least a portion of the projection with the cover in the closed position, and the projection and the receptacle are arranged on corresponding ends of the posts.

12. An anchoring system as in claim 1, wherein the cover includes a first protuberance that projects from the groove in the cover, and the base includes a second protuberance that projects from the groove in the base, the first and second protuberances arranged to cooperate with one another when the cover is closed so as to be capable of capturing a structural portion of the medical article between the first and second protuberances.

13. An anchoring system as in claim 1 additionally comprising a protuberance arranged on the retainer to pin a portion of the catheter within the retainer with the cover in the closed position.

14. An anchoring system as in claim 1, wherein the channel includes a proximal end and a distal end, and the width of the channel, as measured in a lateral direction, is smaller at the proximal end of the channel than at the distal end of the channel.

15. An anchoring system as in claim 14, wherein the width of the channel tapers in a generally linear manner over its length.

16. An anchoring system as in claim 1, wherein at least a portion of the channel includes a width, as measured in a lateral direction, which tapers in size.

17. An anchoring system as in claim 16 additionally comprising a projection extending into the channel, and said portion of the channel, which tapers in width, is formed between the projection and one side wall of the channel.

18. An anchoring system as in claim 17, wherein said channel generally has a Y-shape along its length, which is formed between side walls of the channel and the projection dividing one end of the channel.

19. An anchoring system as in claim 1, wherein at least a portion of the generally curvilinear surface of the base groove has a radius of curvature that is sized to match a radius of a received portion of the medical article.

20. An anchoring system for securing an elongated medical article, comprising:
an anchor pad having an upper surface and a lower surface, at least a portion of the lower surface being formed with an adhesive layer; and
a retainer permanently affixed to the upper surface of the anchor pad, and comprising,
a base having a first generally curvilinear groove to receive at least a portion of the elongated medical article;
a cover being pivotally coupled to the base and moveable between an open position in which the groove is exposed, and a closed position in which the groove is covered, the cover including a second generally curvilinear groove that cooperates with the first groove when the cover is in the closed position to define a channel, the channel being configured to support the portion of the medical article received by the retainer on at least diametrically opposed sides thereof along the entire length of the received portion of the medical article;
at least one retention member projecting into the channel and arranged to be capable of engaging a portion of the medical article to inhibit longitudinal movement of the medical article through the channel; and
the base and the cover including interengaging structure which releasably secures together the base and the cover in the closed position.

21. An anchoring system as in claim 20, wherein the retention member extends generally normal to a longitudinal axis of the channel.

22. An anchoring system as in claim 21, wherein the retention member extends in a radial manner relative to the longitudinal axis of the channel with the longitudinal axis extending through the retention member.

23. An anchoring system as in claim 21, wherein the retention member lies near one longitudinal end of the channel.

24. An anchoring system as in claim 20, wherein the retention member comprises a first protuberance that projects from the groove in the cover, and a second protuberance that projects from the groove in the base.

25. An anchoring system as in claim 24, wherein the first and second protuberances are arranged to cooperate with one another when the cover is closed so as to be capable of capturing a structural portion of the medical article between the first and second protuberances.

26. An anchoring system as in claim 24, wherein the first and second protuberances are diametrically opposed within the channel.

27. An anchoring system as in claim 24, wherein the first and second protuberances include at least one projection and at least one receptacle that receives at least a portion of the projection with the cover in the closed position, said projection and receptacle being arranged on corresponding ends of the first and second protuberances.

28. An anchoring system as in claim 24, wherein the first and second protuberances are positioned near one longitudinal end of the channel.

29. An anchoring system as in claim 20, wherein the retention mechanism comprises a protuberance arranged on the retainer to pin a portion of the catheter within the retainer with the cover in the closed position.

30. An anchoring system as in claim 20, wherein the channel has a generally tapering cross-sectional width, as measured in a lateral direction, and the protuberances are arranged within the channel to divide the channel and to give the channel a generally Y-shape in the longitudinal direction.

31. An anchoring system as in claim 20, wherein said retention member is a friction ridge formed on at least a portion of the surfaces of the grooves in the base and the cover.

32. An anchoring system as in claim 31, wherein the friction ridge is angled toward one longitudinal end of the channel.

33. An anchoring system as in claim 32, wherein the friction ridge has a front wall that forms an acute angle with a surface of the corresponding groove in a longitudinal direction.

34. An anchoring system as in claim 20, wherein said retention member comprises at least one securement barb that is arranged on at least a portion of one of the curvilinear surfaces of the groves on the base and the cover.

35. An anchoring system as in claim 34, wherein the securement barb is angled toward one end of the channel.

36. An anchoring system as in claim 34 additionally comprising a plurality of securement barbs, and at least a portion of the securement barbs being arranged on opposing groove surfaces of the base and the cover in a generally staggered manner.

37. An anchoring system as in claim 36, wherein a least a portion of the securement barbs are angled toward one end of the channel and another portion of the securement barbs are angled toward the other end of the channel.

38. An anchoring system as in claim 36, wherein at least a first securement barb of the plurality of barbs extends from the base groove surface and at least a second securement barb of the plurality of barbs extends from the cover groove surface, and the first and second securement barbs are arranged generally within the same plane that extends generally normal to a longitudinal axis of the channel.

39. An anchoring system as in claim 20, wherein said channel has a width, as measured in a lateral direction, that varies along the longitudinal length of the channel.

40. An anchoring system as in claim 39, wherein the channel includes a proximal end and a distal end, and the cross-sectional width of the channel is smaller at the proximal end than at the distal end.

41. An anchoring system to secure an elongated medical article, comprising an anchor pad having an upper surface and a lower surface, at least a portion of the lower surface formed with an adhesive layer, a base with a first side and a second side, the base including a groove having a curvilinear cross-sectional shape, and a cover with a first side and a second side, the first side of the cover permanently attached to the first side of the base, the second side of the cover detachably securable to the second side of the base and moveable between an open position and a closed position, the cover including a groove which corresponds to the groove in the base, a channel being defined between the grooves of the base and cover when the cover is in the closed position, the channel capable of receiving a portion of the medical article and including retention means for engaging a portion of the medical article to inhibit longitudinal movement of the medical article through the channel, without impairing the fluid flow through the medical article.

42. An anchoring system for an elongated medical article, comprising:

an anchor pad having an upper surface and a lower surface, at least a portion of the lower surface formed with an adhesive layer; and a retainer permanently affixed to the upper surface of the anchor pad, and comprising:

a base having a first groove to receive at least a portion of the elongated medical article;

a cover being pivotally coupled to the base and moveable between an open position and a closed portion, the cover including a second groove that cooperates with the first groove when the cover is in the closed position to define a channel; and a latching mechanism operable between the base and the cover to selectively secure the cover and the base when the cover is in the closed position, the latching mechanism including a pair of bars each formed with a tang, and a pair of notches sized and positioned to receive one of the tangs when the cover is closed, and at least one operator extending from at least one of the bars.

43. An anchoring system as in claim 42, wherein the operator includes an inclined surface that slopes toward the anchor pad in a direction away from the bar.

44. An anchoring system as in claim 42 additionally comprising at least one retention member projecting into the channel and arranged so as to engage a portion of the medical article to inhibit longitudinal movement of the medical article through the channel.

45. An anchoring system as in claim 42, wherein the flexible bar depends from the cover and the notch is formed in the base.

46. An anchoring system as in claim 42, wherein the channel is configured so as to be capable of supporting the portion of the medical article received by the retainer on at least diametrically opposed sides thereof along the entire length of the received portion of the medical article.

47. An anchoring system for securing an elongated medical article, comprising:

an anchor pad having an upper surface and a lower surface, at least a portion of the lower surface being formed with an adhesive layer; and a retainer permanently affixed to the upper surface of the anchor pad, and comprising:

a base having a first generally curvilinear groove to receive at least a portion of the elongated medical article;

a cover being pivotally coupled to the base and moveable between an open position in which the groove is exposed, and a closed position in which the groove is covered, the cover including a second generally curvilinear groove that cooperates with the first groove when the cover is in the closed position to define a channel, the channel being configured to support the portion of the medical article received by the retainer on at least diametrically opposed sides thereof along the entire length of the received portion of the medical article;

at least one retention member projecting into the channel and arranged to be capable of engaging a portion of the medical article to inhibit longitudinal movement of the medical article through the channel, the retention member arranged within the channel to divide the channel and to give the channel a generally Y-shape in the longitudinal direction; and the base and the cover including interengaging structure which releasably secures together the base and the cover in the closed position.

48. An anchoring system for an elongated medical article having at least one inner lumen, the anchoring system comprising an anchor pad having an upper surface and a lower surface, at least a portion of the lower surface being formed with an adhesive layer, and a retainer affixed to the upper surface of the anchor pad, and including a base having a first groove to receive at least a portion of the elongated medical article, a cover being pivotally coupled to the base and moveable between an open position, in which the groove is exposed, and a closed position, in which the groove is covered, the cover including a second groove that cooperates with the first groove when the cover is in the closed position to define a channel, the channel being sized so as to receive a portion of the medical article, the base and the cover including interengaging structure which releasably secures the base and the cover together in the closed position, and a retention mechanism positioned within the channel and including at least first and second members that are arranged to generally oppose and cooperate with one another when the cover is closed so as to be capable of holding a structural portion of the medical article between the first and second members without substantially occluding the inner lumen of the medical article.

49. An anchoring system as in claim 48, wherein the first member include at least one projection that protrudes toward the second member.

50. An anchoring system as in claim 49, wherein the second member includes at least one receptacle that receives at least a portion of the projection with the cover in the closed positions, and the projection and receptacle are arranged on corresponding ends of the first and second members.

51. An anchoring system as in claim 48, wherein the first member comprises a projection and the second member comprises an opposing surface toward which the projection extends.

52. An anchoring system as in claim 51, wherein the second members additionally comprises receptacle formed in the opposing surface, and the receptacle is sized to receive at least a portion of the projection with the cover in the closed position.

53. An anchoring system for securing an elongated medical article to a patient, comprising:

an anchor pad having an upper surface and a lower surface, the lower surface including an adhesive layer on at least a portion of the surface; and a retainer mounted on the upper surface of the anchor pad and capable of receiving a portion of the medical article, the retainer including:

a base having first and second sides, and a groove with a generally curvilinear cross-sectional shape;

a cover having a first side and a second side, the first side of the cover being attached to the first side of the base, and the second side of the cover being movable between a closed position, in which the second side of the cover lies generally above the second side of the base, and an open position, in which the second side of the cover is spaced apart from the second side of the base so as to expose the groove in the base, the cover including a groove having a generally curvilinear cross-sectional shape corresponding in position to the groove in the base to define a channel when the cover lies in the closed position, the defined channel having a curvilinear cross-sectional shape with a cross-sectional area of the channel varying along the length of the channel;

at least one securement barb that is arranged on at least a portion of one of the curvilinear surfaces of the grooves on the base and the cover; and a latching mechanism operable between the base and the cover to releasably secure the second side of the cover to the second side of the base.

54. An anchoring system for securing an elongated medical article to a patient, comprising:

an anchor pad having an upper surface and a lower surface, the lower surface including an adhesive layer on at least a portion of the surface; and a retainer mounted on the upper surface of the anchor pad and capable of receiving a portion of the medical article, the retainer including:

a base having first and second sides, and a groove with a generally curvilinear cross-sectional shape;

a cover having a first side and a second side, the first side of the cover being attached to the first side of the base, and the second side of the cover being movable between a closed position, in which the second side of the cover lies generally above the second side of the base, and an open position, in which the second side of the cover is spaced apart from the second side of the base so as to expose the groove in the base, the cover including a groove having a generally curvilinear cross-sectional shape corresponding in position to the groove in the base to define a channel when the cover lies in the closed position, the defined channel having a curvilinear cross-sectional shape with a cross-sectional area of the channel varying along the length of the channel;

a first post which is located at least near the channel and extends generally normal to a longitudinal axis of the channel;

a second post arranged to oppose the first post with one of the posts located on the cover and the other post located on the base; and a latching mechanism operable between the base and the cover to releasably secure the second side of the cover to the second side of the base, wherein one of the posts includes at least one projection that protrudes toward the other post, and the other post includes at least one receptacle that receives at least a portion of the projection with the cover in the closed position, and the projection and the receptacle are arranged on corresponding ends of the posts.

55. An anchoring system for securing an elongated medical article to a patient, comprising:

an anchor pad having an upper surface and a lower surface, the lower surface including an adhesive layer on at least a portion of the surface; and a retainer mounted on the upper surface of the anchor pad and capable of receiving a portion of the medical article, the retainer including:

a base having first and second sides, and a groove with a generally curvilinear cross-sectional shape;

a cover having a first side and a second side, the first side of the cover being attached to the first side of the base, and the second side of the cover being movable between a closed position, in which the second side of the cover lies generally above the second side of the base, and an open position, in which the second side of the cover is spaced apart from the second side of the base so as to expose the groove in the base, the cover including a groove having a generally curvilinear cross-sectional shape corresponding in position to the groove in the base to define a channel when the cover lies in the closed position, the defined channel having a curvilinear cross-sectional shape with a cross-sectional area of the channel varying along the length of the channel, wherein the channel includes a proximal end and a distal end, and the width of the channel, as measured in a lateral direction, is smaller at the proximal end of the channel than at the distal end of the channel; and a latching mechanism operable between the base and the cover to releasably secure the second side of the cover to the second side of the base.

56. An anchoring system for securing an elongated medical article to a patient, comprising:

an anchor pad having an upper surface and a lower surface, the lower surface including an adhesive layer on at least a portion of the surface; and a retainer mounted on the upper surface of the anchor pad and capable of receiving a portion of the medical article, the retainer including:

a base having first and second sides, and a groove with a generally curvilinear cross-sectional shape;

a cover having a first side and a second side, the first side of the cover being attached to the first side of the base, and the second side of the cover being movable between a closed position, in which the second side of the cover lies generally above the second side of the base, and an open position, in which the second side of the cover is spaced apart from the second side of the base so as to expose the groove in the base, the cover including a groove having a generally curvilinear cross-sectional shape corresponding in position to the groove in the base to define a channel when the cover lies in the closed position, the defined channel having a curvilinear cross-sectional shape with a cross-sectional area of the channel varying along the length of the channel, and wherein at least a portion of the channel includes a width, as measured in a lateral direction, which tapers in size;

a projection extending into the channel, said portion of the channel which tapers in width being formed between the projection and one side wall of the channel, and said channel generally having a Y-shape along its length, the projection dividing one end of the channel; and a latching mechanism operable between the base and the cover to releasably secure the second side of the cover to the second side of the base.

57. An anchoring system for securing an elongated medical article, comprising:

an anchor pad having an upper surface and a lower surface, at least a portion of the lower surface being formed with an adhesive layer; and a retainer permanently affixed to the upper surface of the anchor pad, and comprising:

a base having a first generally curvilinear groove to receive at least a portion of the elongated medical article;

a cover being pivotally coupled to the base and moveable between an open position in which the groove is exposed, and a closed position in which the groove is covered, the cover including a second generally curvilinear groove that cooperates with the first groove when the cover is in the closed position to define a channel, the channel being configured to support the portion of the medical article received by the retainer on at least diametrically opposed sides thereof along the entire length of the received portion of the medical article, wherein the channel includes a proximal end and a distal end, and the cross-sectional width of the channel is smaller at the proximal end than at the distal end;

at least one retention member projecting into the channel and arranged to be capable of engaging a portion of the medical article to inhibit longitudinal movement of the medical article through the channel; and the base and the cover including interengaging structure which releasably secures together the base and the cover in the closed position.

58. An anchoring system for securing an elongated medical article, comprising:

an anchor pad having an upper surface and a lower surface, at least a portion of the lower surface being formed with an adhesive layer; and a retainer permanently affixed to the upper surface of the anchor pad, and comprising:

a base having a first generally curvilinear groove to receive at least a portion of the elongated medical article;

a cover being pivotally coupled to the base and moveable between an open position in which the groove is exposed, and a closed position in which the groove is covered, the cover including a second generally curvilinear groove that cooperates with the first groove when the cover is in the closed position to define a channel, the channel being configured to support the portion of the medical article received by the retainer on at least diametrically opposed sides thereof along the entire length of the received portion of the medical article;

at least one securement barb that is arranged on at least a portion of one of the curvilinear surfaces of the grooves on the base and the cover, the securement barb arranged to be capable of engaging a portion of the medical article to inhibit longitudinal movement of the medical article through the channel; and the base and the cover including interengaging structure which releasably secures together the base and the cover in the closed position.

* * * * *

UNITED STATES PATENT AND TRADEMARK OFFICE
CERTIFICATE OF CORRECTION

PATENT NO. : 6,283,945 B1 Page 1 of 1
DATED : September 4, 2001
INVENTOR(S) : Steven F. Bierman It is certified that error appears in the above-identified patent and that said Letters Patent is hereby corrected as shown below:

Column 20,
Line 18, please delete "arc" and insert therefore, -- are --.

Signed and Sealed this

Twenty-first Day of June, 2005

JON W. DUDAS
*Director of the United States Patent and Trademark Office*